US010898540B2

(12) United States Patent
Kim et al.

(10) Patent No.: US 10,898,540 B2
(45) Date of Patent: Jan. 26, 2021

(54) PEPTIDE HAVING EFFECTS OF INCREASING TELOMERASE ACTIVITY AND EXTENDING TELOMERE, AND COMPOSITION CONTAINING SAME

(71) Applicants: GEMVAX & KAEL CO., LTD., Daejeon (KR); Sang Jae Kim, Seoul (KR)

(72) Inventors: Sang Jae Kim, Seoul (KR); Kyuyong Lee, Gyeonggi-do (KR); Seong Ho Koh, Gyeonggi-do (KR)

(73) Assignee: Gem Vax & KAEL Co., Ltd., Daejeon (KR)

( * ) Notice: Subject to any disclaimer, the term of this patent is extended or adjusted under 35 U.S.C. 154(b) by 0 days.

(21) Appl. No.: 16/091,674

(22) PCT Filed: Apr. 7, 2017

(86) PCT No.: PCT/KR2017/003815
§ 371 (c)(1),
(2) Date: Oct. 5, 2018

(87) PCT Pub. No.: WO2017/176087
PCT Pub. Date: Oct. 12, 2017

(65) Prior Publication Data
US 2019/0142894 A1 May 16, 2019

(30) Foreign Application Priority Data
Apr. 7, 2016 (KR) .................. 10-2016-0042915

(51) Int. Cl.
*A61K 38/10* (2006.01)
*C07K 7/08* (2006.01)
*A61K 8/64* (2006.01)
*A61Q 19/00* (2006.01)
*A23L 33/18* (2016.01)

(52) U.S. Cl.
CPC .............. *A61K 38/10* (2013.01); *A23L 33/18* (2016.08); *A61K 8/64* (2013.01); *A61Q 19/00* (2013.01); *C07K 7/08* (2013.01)

(58) Field of Classification Search
None
See application file for complete search history.

(56) References Cited

U.S. PATENT DOCUMENTS

| 6,967,211 | B2 | 11/2005 | Inoue |
| 7,030,211 | B1 | 4/2006 | Gaudernack et al. |
| 7,786,084 | B2 | 8/2010 | Benner et al. |
| 7,794,723 | B2 | 9/2010 | Gaudernack et al. |
| 8,828,403 | B2 | 9/2014 | Filaci et al. |
| 8,933,197 | B2 | 1/2015 | Bogin et al. |
| 9,023,987 | B2 | 5/2015 | Chung et al. |
| 9,540,419 | B2 | 1/2017 | Kim et al. |
| 9,572,858 | B2 | 2/2017 | Kim et al. |
| 9,907,837 | B2 | 3/2018 | Kim et al. |
| 9,907,838 | B2 | 3/2018 | Kim et al. |
| 9,937,240 | B2 | 4/2018 | Kim et al. |
| 10,039,811 | B2 | 8/2018 | Kim et al. |
| 2002/0042401 | A1 | 4/2002 | Ferguson et al. |
| 2003/0027769 | A1 | 2/2003 | Scialdone et al. |
| 2003/0143228 | A1 | 7/2003 | Chen et al. |
| 2006/0040307 | A1 | 2/2006 | Cech et al. |
| 2006/0106196 | A1 | 5/2006 | Gaudernack et al. |
| 2007/0190561 | A1 | 8/2007 | Morin et al. |
| 2008/0025986 | A1 | 1/2008 | Ozes et al. |
| 2009/0136917 | A1 | 5/2009 | Szalay et al. |
| 2009/0186802 | A1 | 7/2009 | Alluis et al. |
| 2009/0215852 | A1 | 8/2009 | Bascomb et al. |
| 2010/0003229 | A1 | 1/2010 | Santos |
| 2011/0135692 | A1 | 6/2011 | Filaci et al. |
| 2011/0150873 | A1 | 6/2011 | Grainger |
| 2011/0183925 | A1 | 7/2011 | Sato et al. |
| 2012/0065124 | A1 | 3/2012 | Morishita et al. |
| 2012/0208755 | A1 | 8/2012 | Leung |
| 2012/0277290 | A1 | 11/2012 | Collard et al. |

(Continued)

FOREIGN PATENT DOCUMENTS

| CN | 1313773 A | 9/2001 |
| EP | 1020190 A3 | 10/2000 |

(Continued)

OTHER PUBLICATIONS

Albini, A., et al., "Cancer Prevention by Targeting Angiogenesis," Nature reviews Clinical oncology 9(9):498-509, Nature Pub Group (2012).
Altschul, S.F., et al., "Basic Local Alignment Search Tool," Journal of Molecular Biology 215(3):403-410, Elsevier, England (Oct. 1990).
Auerbach, R., et al., "Angiogenesis Assays: Problems and Pitfalls," Cancer Metastasis Reviews 19(1-2):167-172, Kluwer Academic, Netherlands (2000).
Beer, T.M., et al., "Phase II Study of Weekly Docetaxel in Symptomatic Androgen-independent Prostate Cancer," Annals of Oncology 12(9):1273-1279, Oxford University Press, England (2001).

(Continued)

*Primary Examiner* — John D Ulm
(74) *Attorney, Agent, or Firm* — Sterne, Kessler, Goldstein & Fox P.L.L.C.

(57) ABSTRACT

The present specification relates to a composition containing a peptide having effects of increasing telomerase activity and extending a telomere, and more specifically, to a composition containing a telomerase-derived peptide, thereby being effective for preventing, alleviating and treating diseases, caused by a decrease in telomerase activity or a reduction in telomere length, and symptoms caused by cell aging or damage. According to one aspect to the present invention, the peptide increases telomerase activity and is effective for extending a telomere, and thus a method for treating diseases induced by an abnormal decrease in telomerase activity and by the length reduction or loss of a telomere and alleviating symptoms caused thereby can be provided.

6 Claims, 3 Drawing Sheets

Specification includes a Sequence Listing.

(56) References Cited

U.S. PATENT DOCUMENTS

| | | |
|---|---|---|
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim et al. |
| 2015/0307859 A1 | 10/2015 | Kim |
| 2015/0343095 A1 | 12/2015 | Kim et al. |
| 2016/0002613 A1 | 1/2016 | Kim et al. |
| 2016/0008438 A1 | 1/2016 | Kim et al. |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim et al. |
| 2016/0296604 A1 | 10/2016 | Kim et al. |
| 2016/0375091 A1 | 12/2016 | Kim |
| 2017/0028035 A1 | 2/2017 | Kim et al. |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 12/2017 | Kim |
| 2018/0036384 A1 | 2/2018 | Kim |
| 2018/0207241 A1 | 7/2018 | Kim |
| 2018/0318383 A1 | 11/2018 | Kim et al. |
| 2019/0030137 A1 | 1/2019 | Kim et al. |
| 2019/0032032 A1 | 1/2019 | Kim |
| 2019/0142894 A1 | 5/2019 | Kim et al. |

FOREIGN PATENT DOCUMENTS

| | | |
|---|---|---|
| EP | 1093381 B2 | 7/2009 |
| EP | 1817337 B1 | 1/2011 |
| EP | 2871235 A1 | 5/2015 |
| EP | 3333180 A1 | 6/2018 |
| JP | 2002520293 A | 7/2002 |
| JP | 2002522373 A | 7/2002 |
| JP | 2010252810 A | 11/2010 |
| JP | 2011515498 A | 5/2011 |
| JP | 2012500279 A | 1/2012 |
| JP | 2012526524 A | 11/2012 |
| JP | 5577472 B2 | 8/2014 |
| KR | 19930001915 A | 2/1993 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060065588 A | 6/2006 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120035150 A | 4/2012 |
| KR | 20120087885 A | 8/2012 |
| KR | 20120121196 A | 11/2012 |
| KR | 20120130996 A | 12/2012 |
| KR | 20120133661 A | 12/2012 |
| KR | 20130004949 A | 1/2013 |
| KR | 20130041896 A | 4/2013 |
| KR | 20140037698 A | 3/2014 |
| KR | 20140104288 A | 8/2014 |
| KR | 20140140396 A | 12/2014 |
| KR | 20150128336 A | 11/2015 |
| WO | WO-0002581 A1 | 1/2000 |
| WO | WO-0007565 A2 | 2/2000 |
| WO | WO-2008149345 A2 | 12/2008 |
| WO | WO-2009025871 A1 | 2/2009 |
| WO | WO-2009120914 A1 | 10/2009 |
| WO | WO-2010003520 A2 | 1/2010 |
| WO | WO-2010012850 A1 | 2/2010 |
| WO | WO-2010022125 A1 | 2/2010 |
| WO | WO-2010128807 A2 | 11/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167298 A1 | 11/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014012683 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014046983 A1 | 3/2014 |
| WO | WO-2014130909 A1 | 8/2014 |
| WO | WO-2014171792 A1 | 10/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |
| WO | WO-2016105086 A1 | 6/2016 |
| WO | WO-2016137162 A1 | 9/2016 |
| WO | WO-2017078440 A1 | 5/2017 |

OTHER PUBLICATIONS

Berendsen, H.J., "A Glimpse of the Holy Grail?," Science 282(5389):642-643, American Association for the Advancement of Science, United States (1998).

Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).

Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).

Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).

Brandenburg, K., et al., "Peptide-based Treatment of Sepsis," Applied Microbiology and Biotechnology 90(3):799-808, Springer International, Germany (2011).

Bruns, A.F., et al., "A Heat-shock Protein Axis Regulates VEGFR2 Proteolysis, Blood Vessel Development and Repair," PloS One 7(11):e48539, Public Library of Science, United States (2012).

Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).

Calderwood, S.K., et al., "Heat Shock Proteins in Cancer: Chaperones of Tumorigenesis," Trends in Biochemical Sciences 31(3):164-172, Elsevier Trends Journals, England (2006).

Cho, Y.J., "GemVax & Kael (082270)," Hana Daetoo Securities, Company Report, Sep. 10, 2012, 9 pages.

Choi, S.G., "Recent Advances in Cancer Cachexia," Journal of Korean Oncology Nursing 11(1):20-25 (2011).

ClinicalTrials.gov, "Adjuvant Leuprolide with or without Docetaxel in High Risk Prostate Cancer After Radial Prostatectomy," Identifier

(56) References Cited

OTHER PUBLICATIONS

NCT00283062, first received on Jan. 26, 2006, accessed at https://clinicaltrials.gov/ct2/show/study/NCT00283062, last accessed on May 12, 2017, 7 pages.
ClinicalTrials.gov, "Gemcitabine, Capecitabine, and Telomerase Peptide Vaccine GV1001 in Treating Patients With Locally Advanced and Metastatic Pancreatic Cancer," Identifier NCT00425360, accessed at https://clinicaltrials.gov/archive/NCT00425360/2007_01_22, last accessed on Apr. 7, 2017, 4 pages.
Co-pending U.S. Appl. No. 15/772,928, inventors Kim, S.J., et al., filed on Nov. 3, 2016 (Not Published).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
De Araujo, J.G., et al., "The Potential Use of Melatonin for Preventing Cisplatin Ototoxicity: An Insight for a Clinical Approach," Advances in Otolaryngology 2014:8 pages, Hindawi Publishing Corporation (2014).
Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.
Dementia from Merck Manual, accessed on Jul. 29, 2009, pp. 1-17.
Dempsey, N.C., et al., "Differential Heat Shock Protein Localization in Chronic Lymphocytic Leukemia," Journal of Leukocyte Biology 87(3):467-476, Society for Leukocyte Biology, United States (2010).
Dinarello, C.A., "Interleukin-1 in the Pathogenesis and Treatment of Inflammatory Diseases," Blood 117(14):3720-3732, American Society of Hematology, United States (2011).
Du, C., et al., "Conformational and Topological Requirements of Cell-permeable Peptide Function," The Journal of Peptide Research 51(3):235-243, Munksgaard, Denmark (1998).
Du, R., et al., "HIF1 alpha Induces the Recruitment of Bone Marrow-derived Vascular Modulatory Cells to Regulate Tumor Angiogenesis and Invasion," Cancer Cell 13(3):206-220, Cell Press, United States (2008).
Eisenegger, C., et al., "The Role of Testosterone in Social Interaction," Trends in Cognitive Sciences 15(6):263-271, Elsevier Science, England (2011).
Engineer, D.R. and Garcia, J.M., "Leptin in Anorexia and Cachexia Syndrome," International Journal of Peptides 2012:Article ID 287457, Hindawi Publishing Corporation, United States (2012).
"Seoul National University Bundang Hospital excited because of '000'," Clinical trials of Dream Anticancer Drug without side effects with Kael & GemVax, 4 pages, Apr. 22, 2013.
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Extended European Search Report for Application No. EP14808179, dated May 24, 2017, 24 pages.
Fauce, S.R., et al., "Telomerase-Based Pharmacologic Enhancement of Antiviral function of Human CD8+ T Lymphocytes," Immunology 181(10):7400-7406, American Association of Immunologists, United States (Nov. 2008).
Ferrarini, M., et al., "Unusual Expression and Localization of Heat-shock Proteins in Human Tumor Cells," International Journal of Cancer 51(4):613-619, Wiley-Liss, United States (1992).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fontanes, V., et al., "A cell permeable peptide inhibits Hepatitis C Virus Replication by Sequestering IRES Transacting Factors," Virology 394(1):82-90, Academic Press, United States (Nov. 2009).
Fried, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.
Fujii, H., et al., "Telomerase Insufficiency in Rheumatoid Arthritis," Proceedings of the National Academy of Sciences USA 106(11):4360-4365, National Academy of Sciences, United States (2009).
Garcia-Carbonero, R., et al., "Inhibition of HSP90 Molecular Chaperones: Moving Into the Clinic," The Lancet Oncology 14(9):e358-e369, Lancet Publishing Group, England (2013).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Guo, R.F., et al., "Regulatory Effects of Eotaxin on Acute Lung Inflammatory Injury," Journal of Immunology 166(8):5208-5218, American Association of Immunologists, United States (2001).
Heitz, F., et al., "Twenty Years of Cell-Penetrating Peptides: From Molecular Mechanisms to Therapeutics," British Journal of Pharmacology 157(2):195-206, Wiley, England (2009).
Heldin, C.H., et al., "TGF-Beta Signalling from Cell Membrane to Nucleus through SMAD Proteins," Nature 390(6659):465-471, Nature Publishing Group, England (1997).
Henry, J.Y., et al., "Lenalidomide Enhances the Anti-prostate Cancer Activity of Docetaxel in vitro and in vivo," The Prostate 72(8):856-867, Wiley-Liss, United States (2012).
Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor and Francis, United States (2012).
International Preliminary Report on Patentability and Written Opinion for International Application No. PCT/KR2015/014099, The International Bureau of WIPO, dated Jun. 27, 2017, 16 pages.
International Preliminary Report on Patentability and Written Opinion for International Application No. PCT/KR2016/001646, Korean Intellectual Property Office, Republic of Korea, dated May 20, 2016, 13 pages.
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Preliminary Report on Patentability for International Application No. PCT/KR2014/011280, The International Bureau of WIPO, Geneva, Switzerland, dated May 24, 2016, 15 pages.
International Preliminary Report on Patentability for International Application No. PCT/KR2014/012502, The International Bureau of WIPO, Geneva, Switzerland, dated Jun. 21, 2016, 22 pages.

(56) References Cited

OTHER PUBLICATIONS

International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014, 14 pages.
International Preliminary Report on Patentability for International Application No. PCT/KR2013/004176, The International Bureau of WIPO, Switzerland, dated Nov. 11, 2014, 14 pages.
International Preliminary Report on Patentability for International Application No. PCT/KR2013/006218, The International Bureau of WIPO, Switzerland, dated Jan. 13, 2015, 27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Application No. PCT/KR2014/010035, Korean Intellectual Property Office, Republic of Korea, dated Apr. 26, 2016, 13 pages.
International Preliminary Report on Patentability for International Patent Application No. PCT/KR2013/004156, The International Bureau of WIPO, Geneva, Switzerland, dated Nov. 11, 2014, 15 pages.
International Search Report and Written Opinion for International Application No. PCT/KR2016/012613, Korean Intellectual Property Office, Republic of Korea, dated Feb. 2, 2017, 14 pages.
International Search Report for Application No. PCT/KR2016/007192, dated Sep. 12, 2016, 12 pages.
International Search Report for International Application No. PCT/KR2014/003425, Korean Intellectual Property Office, Republic of Korea, dated Jul. 21, 2014, 8 pages.
International Search Report for International Application No. PCT/KR2014/011280, Korean Intellectual Property Office, Republic of Korea, dated Feb. 11, 2015, 12 pages.
International Search Report for International Application No. PCT/KR2014/012502, Korean Intellectual Property Office, Republic of Korea, dated Mar. 11, 2015, 10 pages.
International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 20, 2016, 8 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2013/008459, Korean Intellectual Property Office, Republic of Korea, dated Dec. 23, 2013, 8 pages.
International Search Report for International Application No. PCT/KR2014/004752, Korean Intellectual Property Office, Republic of Korea, dated Jan. 16, 2015, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Application No. PCT/KR2015/003642, Korean Intellectual Property Office, Republic of Korea, dated Jul. 3, 2015, 8 pages.
International Search Report for International Patent Application No. PCT/KR2013/004156, Korean Intellectual Property Office, Republic of Korea, dated Aug. 14, 2013, 10 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jain, R.K., "Barriers to Drug Delivery in Solid Tumors," Scientific American 271(1):58-65, Scientific American, Inc., United States (Jul. 1994).
Jemal, A., et al., "Cancer Statistics, 2008," CA: A Cancer Journal for Clinicians 58(2):71-96, Wiley, United States (2008).
Kalnins, A., et al., "Sequence of the Lacz Gene of *Escherichia coli*," The EMBO Journal 2(4):593-597, Wiley Blackwell, England (1983).
Kawasaki, H., et al., "Detection and Evaluation of Activation of Various Cancer Antigenic Peptide-specific CTLs in Mature Dendritic Cells Used for Dendritic Cell Therapy," The21st International Congress of Personalized Medicine, Conference Program and Abstracts, Personalized Medicine Universe (Japanese edition) 4(Supplement 2): 2 pages, Oct. 17, 2015.
Kern, K.A. and Norton, J.A., "Cancer Cachexia," Journal of Parenteral and Enteral Nutrition 12(3):286-298, Sage Publications, United States (1988).
Kim, B.H., "Presbycusis: Review for its Environmental Risk Factors," Korean Journal of Otorhinolaryngology-Head and Neck Surgery 49(10):962-967, Korean Society of Otolaryngology-Head and Neck Surgery, Korea (2006).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kim, H., et al., "Inhibition of HIV-1 Reactivation by a Telomerase-Derived Peptide in a HSP90-Dependent Manner," Scientific Reports 6: 28896, Nature Publishing Group, England (Jul. 2016).
Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).
Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).
Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).

(56) References Cited

OTHER PUBLICATIONS

Kyte, J.A., et al., "Telomerase Peptide Vaccination Combined with Temozolomide: A Clinical Trial in Stage IV Melanoma Patients," Clinical Cancer Research 17(13):4568-4580,American Association of Cancer Research, United States (2011).

Lahdevirta, J., et al., "Elevated Levels of Circulating Cachectin/ tumor Necrosis Factor in Patients with Acquired Immunodeficiency Syndrome," American Journal of Medicine 85(3):289-291, Excerpta Medica, United States (1988).

Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).

Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015).

Lee, S.A., et al., "A Telomerase-Derived Peptide Regulates Reactive Oxygen Species and Hepatitis C Virus RNA Replication in HCV-Infected Cells Via Heat Shock Protein 90," Biochemical and Biophysical Research Communications 471(1):156-162, Elsevier, United States (Feb. 2016).

Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).

Leem G., et al., Immunotherapy in Pancreatic Cancer; the Road Less Traveled Immunol Disord Immunotherapy, Jun. 26, 2016 (Jun. 26, 2016), p. 1000106, XP055328627, Retrieved from the Internet: (URL:http://www.omicsgroup.orgjjournalsjimmunotherapy-in-pancreatic-cancer-the-road-less-traveled-IDIT-1000104.pdf).

Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).

Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).

Mandal, A., "Types of Fibrosis," Retrieved from the internet on Jul. 3, 2014, pp. 1-3.

Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).

Massague, J., "Tgf-Beta Signal Transduction," Annual Review of Biochemistry 67:753-791, Annual Reviews, United States (1998).

Mattson, M.P., "Pathways Towards and Away From Alzheimer's Disease," Nature 430(7000):631-639, Nature Publishing Group, England (2004).

McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).

Merck Manual: Respiratory Diseases, Medical Topics, accessed on Nov. 2, 2017, pp. 1-4.

Merck, "Obesity, The Merck Manual Professional Edition," accessed at https://www.merckmanuals.com/professional/nutritional-disorders/obesity-and-the-metabolic-syndrome/obesity, accessed on Oct. 6, 2014, 9 pages.

Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet. Oncology 15(8):829-840, Lancet Pub. Group, England (2014).

Middleton, G.W., "A Phase III Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL: http://meetinglibrary.asco.orgjcontent/82894?media=vm).

Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013)-(Jun. 4, 2013), XP055328310.

Middleton, G.W., et al., Poster: Predictive Cytokine Biomarkers for Survival in Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun. 3, 2014), pp. 1-1. XP055328448. Retrieved from the Internet: (URL:http://media4.asco.org/144/8599/93976/93976_poster_pvhr.jpg).

Modica-Napolitano, J.S. and Singh, K.K., "Mitochondria as Targets for Detection and Treatment of Cancer," Expert Reviews in Molecular Medicine 4(9):1-19, Cambridge University Press, England (2002).

Morano, K.A., "New Tricks for an Old Dog: the Evolving World of Hsp70," Annals of the New York Academy of Sciences 1113:1-14, Blackwell, United States (2007).

Morishita, M., and Peppas, N.A., "Is the Oral Route Possible for Peptide and Protein Drug Delivery?," Drug Discovery Today 11(19-20):905-910, Elsevier Science Ltd., England (2006).

Murphy, M.E., "The Hsp70 Family and Cancer," Carcinogenesis 34(6):1181-1188, Irl Press, England (2013).

Myers, L.K., et al., "Collagen-Induced Arthritis, an Animal Model of Autoimmunity," Life Sciences 61(19):1861-1878, Elsevier, Netherlands (1997).

Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).

National Center for Biotechnology Information, "Hormones," MeSH Database, Bethesda, accessed at http://www.ncbi.nlm.nih.gov/mesh/68006728, accessed on May 8, 2017, 3 pages.

National Horizon Scanning Centre News on Emerging Technologies in Healthcare, GV1001 for Advanced and/or Metastatic Pancreatic Cancer, Published Apr. 2008.

National Institute of Diabetes and Digestive and Kidney Diseases, "Prostate Enlargement: Benign Prostatic Hyperplasia," accessed at https://www.niddk.nih.gov/health-information/urologic-diseases/prostate-problems/prostate-enlargement-benign-prostatic-hyperplasia, accessed Sep. 2014, 14 pages.

Nawroth, I., et al., "Intraperitoneal Administration of Chitosan/DsiRNA Nanoparticles Targeting TNFα Prevents Radiation-induced Fibrosis," Radiotherapy and Oncology 97(1):143-148, Elsevier Scientific Publishers, Ireland (2010).

NCBI, Reference Sequence: XP_003776612.1 (Jul. 17, 2012).

Neoptolemos J.P., et al., "Predictive 1-20 Cytokine Biomarkers for Survival in Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial," 2014 ASCO Annual Meeting, May 30, 2014 (May 30, 2014)-Jun. 3, 2014 (Jun. 3, 2014), pp. 1-3.

Ngo. et al., "Computational Complexity, Protein Structure Prediction, and the Levinthal Paradox," in the Protein Folding Problem and Tertiary Structure Prediction, Merz, Jr., K.M., and Le Grand, S.M., eds., pp. 491-494, Birkhauser Boston, United States (1994).

Novina, C.D. and Sharp, P.A., "The RNAi Revolution," Nature 430(6996):161-164, Nature Publishing Group, England (2004).

O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).

Oh, H., et al., "Telomerase Reverse Transcriptase Promotes Cardiac Muscle Cell Proliferation, Hypertrophy, and Survival," Proceedings of the National Academy of Sciences USA 98(18):10308-10313, National Academy of Sciences, United States (2001).

(56) References Cited

OTHER PUBLICATIONS

Olney, J.W., et al., "Pathological Changes Induced in Cerebrocortical Neurons by Phencyclidine and Related Drugs," Science 244(4910):1360-1362, American Association for the Advancement of Science, United States (Jun. 1989).
Ortega, V.E., "Asthma," Merck manual, accessed at http://www.merckmanuals.com/professional/pulmonary-disorders/asthma-and-related-disorders/asthma, accessed on Nov. 2, 2017, pp. 1-19.
Pearson, W.R. and Lipman, D.J., "Improved Tools for Biological Sequence Comparison," Proceedings of the National Academy of Sciences of the United States of America 85(8):2444-2448, National Academy of Sciences, United States (Apr. 1988).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Priya, S.G., et al., "Skin Tissue Engineering for Tissue Repair and Regeneration," Tissue Engineering. Part B, Reviews 14(1):105-118, Mary Ann Liebert, Inc., United States (2008).
Rana, T.M., "Illuminating the Silence: Understanding the Structure and Function of Small RNAs," Nature Reviews. Molecular Cell Biology 8(1):23-36, Nature Publishing Group, England (2007).
Rheumatoid Arthritis from Merck Manual, accessed on Apr. 21, 2016, pp. 1-18.
Rosenbloom, J., et al., "Strategies for Anti-fibrotic Therapies," Biochimica et Biophysica Acta 1832(7):1088-1103, Elsevier Pub. Co., Netherlands (2013).
Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.
Roubenoff, R., et al., "Adjuvant Arthritis as a Model of Inflammatory Cachexia," Arthritis and Rheumatism 40(3):534-539, Wiley-Blackwell, United States (1997).
Rowe-Rendleman, C. and Glickman, R.D., "Possible therapy for age-related macular degeneration using human telomerase," Brain Research Bulletin 62(6):549-553, Elsevier Science Inc., United States (2004).
Rudinger, J., "Characteristics of the Amino Acids as Components of a Peptide Hormone Sequence," in Peptide Hormones, Parsons, J.A., ed., University Park Press, United States (1976).
Sasada, A., et al., "A Case of Elderly Patient With Lung Cancer Efficiently Treated With Dendritic Cell Immunotherapy" The 20th International Congress of Personalized Medicine, Conference Program and Abstracts, Personalized Medicine Universe (Japanese edition) 4(Supplement 1): 2 pages, May 24, 2015.
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Schenk, D., et al., "Immunization with Amyloid-beta Attenuates Alzheimer-disease-like Pathology in the PDAPP Mouse," Nature 400(6740):173-177, Nature Publishing Group, England (1999).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Schwarze, S.R., et al., "In Vivo Protein Transduction: Delivery of a Biologically Active Protein Into the Mouse," Science 285(5433):1569-1572, American Association for the Advancement of Science, United States (1999).
Seo, J.S., et al., "T Cell Lymphoma in Transgenic Mice Expressing the Human Hsp70 Gene," Biochemical and Biophysical Research Communications 218(2):582-587, Elsevier, United States (1996).

Shaw, V.E., et al., "Current Status of GV1001 and Other Telomerase Vaccination Strategies in the Treatment of Cancer," Expert Review of Vaccines 9(9):1007-1016, Taylor & Francis, England (2010).
Shay, J.W., and Wright, W.E., "Telomerase Therapeutics for Cancer: Challenges and New Directions," Nature Reviews. Drug Discovery 5(7):577-584, Nature Publishing Group, England (2006).
SIGMA Genosys, "Designing Custom Peptides," accessed at http://www.sigma-genosys.com/peptide_design.asp, Accessed on Dec. 16, 2004, 2 pages.
Smith, D.B. and Johnson, K.S., "Single-step Purification of Polypeptides Expressed in *Escherichia coli* as Fusions with Glutathione S-transferase," Gene 67(1):31-40, Elsevier, Netherlands (Jul. 1988).
Smith, T.F. and Waterman, M.S., "Comparison of Biosequences," Advances in Applied Mathematics 2(4):482-489, Academic Press, Inc., United States (Dec. 1981).
Song, J., et al., "Characterization and Fate of Telomerase-Expressing Epithelia during Kidney Repair," Journal of the American Society of Nephrology 22(12):2256-2265, American Society of Nephrology, United States (2011).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.
Stevenson, C.L., "Advances in Peptide Pharmaceuticals," Current Pharmaceutical Biotechnology 10(1):122-137, Bentham Science Publishers, United Arab Emirates (2009).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Supplemental European Search Report for Application No. EP14808179, dated Jan. 10, 2017, 13 pages.
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "CLUSTAL W: Improving the Sensitivity of Progressive Multiple Sequence Alignment through Sequence Weighting, Position-specific Gap Penalties and Weight Matrix Choice," Nucleic Acids Research 22(22):4673-4680, Oxford University Press, England (Nov. 1994).
Tisdale, M.J., "Catabolic Mediators of Cancer Cachexia," Current Opinion in Supportive and Palliative Care, 2(4):256-261, Lippincott Williams & Wilkins, United States (2008).
Tisdale, M.J., "Mechanisms of Cancer Cachexia," Physiological Reviews 89(2):381-410, American Physiological Society, United States (2009).
Tomari Y. and Zamore, P.D., "Perspective: Machines for RNAi," Genes and Development 19(5):517-529, Cold Spring Harbor Laboratory Press, United States (2005).
Uehara, Y., "Natural Product Origins of Hsp90 Inhibitors," Current Cancer Drug Targets 3(5):325-330, Bentham Science Publishers, Netherlands (2003).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Apr. 2011).
Vennela, B., et al., "Current and Future Strategies for Therapy of Pancreatic Cancer," International Journal of Research in Pharmacy and Medicine 2(3):728-740 (2012).

(56) References Cited

OTHER PUBLICATIONS

Voet, D. and Voet, J.G., "Abnormal Hemoglobins," in Biochemistry, 2nd Edition, Chapter 9, pp. 235-241, John Wiley & Sons, Inc., United States (1995).
Volloch, V.Z. and Sherman, M.Y., "Oncogenic Potential of Hsp72," Oncogene 18(24):3648-3651, Nature Publishing Group, England (1999).
Walsmith, J. and Roubenoff, R., "Cachexia in Rheumatoid Arthritis," International Journal of Cardiology 85(1):89-99, Elsevier, Netherlands (2002).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).
Written opinion for Application No. PCT/KR2016/007192, dated Sep. 12, 2016, 16 pages.
Written Opinion for International Application No. PCT/KR2014/003425, Korean Intellectual Property Office, Republic of Korea, dated Jul. 21, 2014, 13 pages.
Written Opinion for International Application No. PCT/KR2014/011280, Korean Intellectual Property Office, Republic of Korea, dated Feb. 11, 2015, 14 pages.
Written Opinion for International Application No. PCT/KR2014/012502, Korean Intellectual Property Office, Republic of Korea, dated Mar. 11, 2015, 20 pages.
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2013/008459, Korean Intellectual Property Office, Republic of Korea, dated Dec. 23, 2013, 9 pages.
Written Opinion for International Application No. PCT/KR2014/004752, Korean Intellectual Property Office, Republic of Korea, dated Jan. 16, 2015, 21 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2014/010035, Korean Intellectual Property Office, Republic of Korea, dated Feb. 2, 2015, 11 pages.
Written Opinion for International Application No. PCT/KR2015/003642, Korean Intellectual Property Office, Republic of Korea, dated Jul. 3, 2015, 16 pages.
Written Opinion for International Patent Application No. PCT/KR2013/004156, Korean Intellectual Property Office, Republic of Korea, dated Aug. 14, 2013, 13 pages.
Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Yeh, C.H., et al., "Clinical Correlation of Circulating Heat Shock Protein 70 in Acute Leukemia," Leukemia Research 34(5):605-609, Pergamon Press, England (2010).
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).
Zhou, J., et al., "PI3K/Akt Is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Petrylak D.P., "The Treatment of Hormone-Refractory Prostate Cancer: Docetaxel and Beyond," Reviews in Urology 8 (Supp) 2): S48-S55, United States (2006).
Shay, J.W., and Keith, W.N., "Targeting Telomerase for Cancer Therapeutics," in: British Journal of Cancer 98(4):677-683, Nature Publishing Group on behalf of Cancer Research UK (2008).
Hey, Y.Y and O'Neill, H.C., "Murine spleen contains a diversity of myeloid and dendritic cells distinct in antigen presenting function," Journal of Cellular and Molecular Medicine, 16(11):2611-2619, Wiley-Blackwell, England (Nov. 2012).
Tarantino, G., et al. "Spleen: a New Role for an Old Player?," World Journal of Gastroenterology, 17(33):3776-3784, Baishideng Publishing Group, United States (Sep. 2011).
International Search Report and Written Opinion of the International Searching Authority directed to related Patent Application No. PCT/KR2017/003815, dated Jul. 10, 2017; 12 pages.
International Preliminary Report on Patentability of the International Searching Authority directed to related Application No. PCT/KR2017/003815, dated Oct. 9, 2018; 9 pages.
Khavinson et al., "Epithalon Peptide Induces Telomerase Activity and Telomere Elongation in Human Somatic Cells", Bulletin of Experimental Biology and Medicine, Jun. 2003, vol. 135, No. 6, pp. 590-592.
Simonsen, J.L. et al., "Telomerase expression extends the proliferative life-span and maintains the osteogenic potential of human bone marrow stromal cells," Nat Biotechnol 20 (6): 592-596 (Jan. 2002).
Staff, et al., "Telomerase (GV1001) Vaccination Together with Gemcitabine in Advanced Pancreatic Cancer Patients," International Journal of Oncology 45:1293-1303, Spandidos Publications, United States (2014).
Godet, Y., et al., "Analysis of Spontaneous Tumor-Specific CD4 T-cell Immunity in Lung Cancer Using Promiscuous HLA-DR Telomerase-Derived Epitopes: Potential Synergistic Effect with Chemotherapy Response," *Clinical Cancer Research* 18(10):2943-2953, American Association for Cancer Research Inc., United States (2012).

$$RTA = \frac{[AS-AS,0] / AS, IS}{[ATS8-ATS8,0 / ATSI,IS]} \times 100$$

AS :         Absorbance of sample
AS.0 :      Absorbance of heat – or Rnase-treated sample
AS,IS :      Absorbance of Internal standard [IS] of the sample
ATS8 :     Absorbance of Control template [TS8]
ATS8,0 :    Absorbance of Lysis buffer
ATS8,IS :   Absorbance of Internal standard [IS] of the Control template [TS8]

|  | Time | Temp. | Cycles |
|---|---|---|---|
| Primer elongation | 10 – 30 min | 25°C | 1 |
| Telomerase inacivation |  | 94°C | 94°C |
| Amplification: |  |  |  |
| Denaturation | 30 s | 94°C |  |
| Annealing | 30 s | 50°C | 1 - 30 |
| Polymerization | 90 s | 72°C |  |
|  | 10 min | 72°C | 1 |
| Hold |  | 4°C |  |

FIG. 4

Southern analysis od terminal restriction fragments (TRF)

$$\overline{TRF} = \frac{\sum (Od_i)}{\sum (Od_i / L_i)}$$

$Od_i$ : chemiluminescent signal
$L_i$ : length of the TRF at position 1

FIG. 5

```
                        SEQUENCE LISTING

<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: hTERT derived peptide fragment

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
<213> ORGANISM: homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255
```

```
Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
            290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                    325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                    405                 410                 415

Ala Ala Val Thr Pro Ala Ala Gly Val Cys Ala Arg Glu Lys Pro Gln
                    420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
            450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                    485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
            530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
        610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670
```

-continued

```
Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
```

```
                1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130
```

PEPTIDE HAVING EFFECTS OF INCREASING TELOMERASE ACTIVITY AND EXTENDING TELOMERE, AND COMPOSITION CONTAINING SAME

CROSS-REFERENCE TO RELATED APPLICATIONS

This application is the U.S. national phase of PCT/KR2017/003815, filed Apr. 7, 2017, which claims foreign priority to KR 10-2016-0042915, filed Apr. 7, 2016.

REFERENCE TO SEQUENCE LISTING SUBMITTED ELECTRONICALLY VIA EFS-WEB

The content of the electronically submitted sequence listing (Name: 2473_1030001_st25.TXT; 10,463 bytes; and Date of Creation: Oct. 3, 2018) was originally submitted in the International Application No. PCT/KR2017/003815 and is incorporated herein by reference in its entirety.

BACKGROUND OF THE INVENTION

Technical Field

The specification relates to a peptide having effects of increasing telomerase activity and extending a telomere and a composition including the same, and more particularly, to a composition which includes a peptide derived from telomerase and having an effect of treating or preventing degeneration, aging or death of cells, caused by a decrease in telomerase activity and the loss of a telomere.

Background Art

A telomere, in which a DNA hexamer (TTAGGG) sequence found at the end of a chromosome is repeated, is known to have a function of stabilizing the chromosome. Repeated cell replication shortens the end of a chromosome, which indicates cellular senescence, and therefore, the telomere is an important factor for maintaining the life span of cells in various tissues and is used to evaluate cellular senescence. Telomerase is an enzyme protein that catalyzes the addition of a telomere repeat sequence to the 3' end of a telomere, and serves to restore a telomere lost due to cellular senescence. Telomerase is not expressed in most normal adult cells, a telomere length is gradually decreased in cell replication, and reduction in telomeric repeats leads to cellular senescence.

In specific diseases, the telomeric end is abnormally rapidly lost and leads to aging or degeneration of immature cells. In the case of a human, cells expressing human telomerase (hTERT, human-telomerase reverse transcriptase) are found to bypass a normal cellular senescence pathway. When the expression of telomerase is induced in aged cells having a short telomere, a telomere length is increased, and phenotypes similar to younger cells are restored.

Unlike cancer cells or specific stem cells, somatic cells have little or no telomerase activity, and when ends of some chromosomes including a telomere are shortened to a certain length or less, the cells stop division and go to programmed cellular senescence (cell death). Since the loss of the telomeric repeat sequence is reduced by an increase in telomerase activity, it is expected that the induction of telomerase activity having an effect of adding a telomeric repeat sequence at the end of the telomere restarts the replication and division of somatic cells in a senescent or death phase, and induces restoration of damaged tissue in which a large quantity of the senescent or death-phase cells are distributed.

Additionally, an increase in telomerase activity in somatic cells may help in treating or preventing neurodegenerative diseases (representatively, Alzheimer's disease), treating or improving HIV triggered by premature senescence of immune cells (cytotoxic T lymphocytes) killing infected cells, wound healing such as skin trauma, and maintaining transplanted cells such as bone marrow transplantation. Further, it has been known that the telomerase activity is increased by over-expression of hTERT, which is a part of the telomerase, or expression of a protein regulating the assembly of a telomerase such as a heat-shock protein (HSP).

Estimation of a telomere length is important for understanding the biological and clinical significance of a telomere. The telomere length serves as a useful indicator for research of chromosome stability, telomerase activity and/or expression, proliferative capacity and an aging process of cells. The significance of a clinical value of the telomere may be proved in Bloom syndrome (rare genetic disorder with high frequencies of chromosomal breaks and rearrangement in an infected person), which is a disease induced by cancer, progeria syndrome or partial progeria, genetic abnormality or chromosome instability, and Werner syndrome (rare disorder characterized by the rapid appearance of aging in relatively young people), which is an aging-related disease. The dynamics of the telomere length have unique expression patterns in a certain disease process. Therefore, it is very useful for prediction of a disease.

Meanwhile, as an animal model used in an effectiveness and efficacy experiment for developing drugs for treating a neurodegenerative disease induced by decreases in telomerase activity and telomere length and Alzheimer's disease, which is a well-known neurodegenerative disease, a mouse (3×Tg-AD mouse model) in which three specific genes (APP, Tau, PS1) are modified to accumulate amyloid β and induce a neurofibrillary tangle (NFT) is used. The mouse in which three genes are modified shows progression of a neuronal damage disease including Alzheimer symptoms over time. It has been known that effectiveness and efficacy of drug candidates can be measured by observing inhibition of destruction and regeneration capacity of nerve cells by administering a developed drug to an animal in which loss of the nerve cells is induced and comparing them with those of an untreated control group.

It is known that a peptide PEP1 according to an aspect of the present invention is a peptide consisting of 16 important amino acids present in a catalytic part of telomerase and has anti-inflammatory and antioxidant efficacies. As it has been discovered through animal experiments that the peptide according to an aspect of the present invention is effective in increasing telomerase activity and increasing a telomere length in cells, PEP1 is expected to be effective in prevention and treatment of various diseases induced by decreases in telomerase activity and telomere length.

The specification provides a composition which includes a peptide derived from reverse transcriptase of telomerase to increase telomerase activity and extend a telomere. Specifically, the specification provides a composition including a hTERT-derived peptide to increase telomerase activity and extend a telomere. More specifically, the specification provides a composition including a hTERT-derived peptide consisting of 16 amino acids (PEP1) to increase telomerase activity and extend a telomere.

PRIOR ART LITERATURE

Patent Literature (Patent Literature 1) WO 2008-149345 A2

Non-Patent Literature (Non-Patent Literature 1) Simonsen, J. L. et al., "Telomerase expression extends the proliferative life-span and maintains the osteogenic potential of human bone marrow stromal cells," Nat Biotechnol 20 (6): 592-6 (January, 2002)

BRIEF SUMMARY OF THE INVENTION

Disclosure

Technical Problem

With this background, the inventors had attempted to develop a composition for preventing and treating a symptom caused by decreases in telomerase activity and telomere length to greatly increase telomerase activity and extend a telomere without side effects, and thus the present invention was completed.

An object of the specification provides a peptide composition which is effective, has no side effects, increases telomerase activity and extends a telomere length, and a method of preventing, improving and treating a symptom caused by cellular senescence, damage and death according to decreases in telomerase activity and telomere length.

Technical Solution

In an aspect, the present invention provides a composition including a pharmaceutically effective amount of one or more selected from the group consisting of a peptide comprising an amino acid sequence of SEQ ID NO: 1, a peptide having at least 80% sequence homology with the amino acid sequence and a fragment thereof to increase telomerase activity or extend a telomere length. In another aspect, the present invention provides a method of increasing telomerase activity or extending a telomere length, which includes administering one or more selected from the group consisting of a peptide comprising an amino acid sequence of SEQ ID NO: 1, a peptide having at least 80% sequence homology with the amino acid sequence and a fragment thereof to a subject.

In still another aspect, the present invention provides one or more selected from the group consisting of a peptide comprising an amino acid sequence of SEQ ID NO: 1, a peptide having at least 80% sequence homology with the amino acid sequence and a fragment thereof to increase telomerase activity or extend a telomere length.

In yet another aspect, the present invention provides a use of one or more selected from the group consisting of a peptide comprising an amino acid sequence of SEQ ID NO: 1, a peptide having at least 80% sequence homology with the amino acid sequence and a fragment thereof as an active ingredient for non-therapeutic cosmetics to increase telomerase activity or extend a telomere length.

In yet another aspect, the present invention provides a use of one or more selected from the group consisting of a peptide comprising an amino acid sequence of SEQ ID NO: 1, a peptide having at least 80% sequence homology with the amino acid sequence and a fragment thereof in a composition for increasing telomerase activity or extending a telomere length.

In yet another aspect, the composition is for preventing or treating a disease induced by decreases in telomerase activity and telomere length or a symptom caused by cell loss and senescence.

In yet another aspect, the present invention provides a method of treating or preventing a disease induced by a decrease in telomerase activity or telomere length or a symptom caused by cell loss and senescence, the method including administering one or more selected from the group consisting of a peptide comprising an amino acid sequence of SEQ ID NO: 1, a peptide having at least 80% sequence homology with the amino acid sequence and a fragment thereof to a subject.

In yet another aspect, the present invention provides one or more selected from the group consisting of a peptide comprising an amino acid sequence of SEQ ID NO: 1, a peptide having at least 80% sequence homology with the amino acid sequence and a fragment thereof to be used in treating or preventing a disease induced by a decrease in telomerase activity or telomere length or a symptom caused by cell loss and senescence.

In yet another aspect, the present invention provides a use of one or more selected from the group consisting of a peptide comprising an amino acid sequence of SEQ ID NO: 1, a peptide having at least 80% sequence homology with the amino acid sequence and a fragment thereof as an active ingredient for non-therapeutic cosmetics to improve or prevent a disease induced by a decrease in telomerase activity or telomere length or a symptom caused by cell loss and senescence.

In yet another aspect, the present invention provides a use of one or more selected from the group consisting of a peptide comprising an amino acid sequence of SEQ ID NO: 1, a peptide having at least 80% sequence homology with the amino acid sequence and a fragment thereof in a composition for to improve or prevent a disease induced by a decrease in telomerase activity or telomere length or a symptom caused by cell loss and senescence.

Regarding the composition according to an aspect of the present invention, the disease is one or more selected from a neurodegenerative disorder, a degenerative disease of the nervous system, a degenerative disease of the skeletal system, a degenerative disease of the muscular system, a viral infectious disease, and a genetic disease causing accelerated cell mortality.

Regarding the composition according to an aspect of the present invention, the degenerative disease of the nervous system is any one selected from a brain disease, a spinal cord injury, a peripheral nerve injury, a peripheral nerve disease, amyotrophic lateral sclerosis, dementia, Huntington's disease, Parkinson's disease, Alzheimer's disease, spinal cord cerebellar degeneration, and multiple neuropathy.

Regarding the composition according to an aspect of the present invention, the symptom caused by cell loss and senescence includes one or more selected from tissue loss caused by skin wounds, skin wrinkles, anemia, skin psoriasis, and skin darkening.

According to another aspect of the present invention, a pharmaceutical composition including the composition as an active ingredient is provided to increase telomerase activity or extend a telomere length.

Regarding the pharmaceutical composition according to another aspect of the present invention, the pharmaceutical composition includes a peptide of SEQ ID NO: 1 to be administered at a dose of 0.1 µg/kg to 100 mg/kg.

According to still another aspect of the present invention, a health functional food composition including the composition as an active ingredient is provided to increase telomerase activity or extend a telomere length.

Regarding the health functional food composition according to still another aspect of the present invention, the composition is prepared in any one formulation selected from a powder, a granule, a pill, a tablet, a capsule, a candy, a syrup and a drink.

According to yet another aspect of the present invention, a cosmetic composition including the composition as an active ingredient is provided to increase telomerase activity or extend a telomere length.

Regarding the cosmetic composition according to yet another aspect of the present invention, the cosmetic composition is prepared in any one formulation selected from a skin, a lotion, a cream, a foundation, an essence, a gel, a pack, a foam cleanser, a soap and an ointment for topical use.

Advantageous Effects

A peptide having a sequence of SEQ ID NO: 1, a peptide having a sequence having at least 80% homology with the sequence or a fragment thereof according to the specification is effective in preventing and treating diseases induced by an abnormal decrease in telomerase activity or reduction and loss of a telomere length in cells, a symptom caused by cellular senescence, and diseases associated with the loss of nervous cells and regeneration capability in order to prevent and treat these diseases.

DESCRIPTION OF THE DRAWINGS

FIG. 4 is a table showing experimental conditions on a PCR level in an experiment for measuring telomerase activity.

FIG. 5 is a calculation formula used to analyze an image in an experiment for measuring a telomere length.

DETAILED DESCRIPTION OF THE INVENTION

Modes of the Invention

Figure 1:
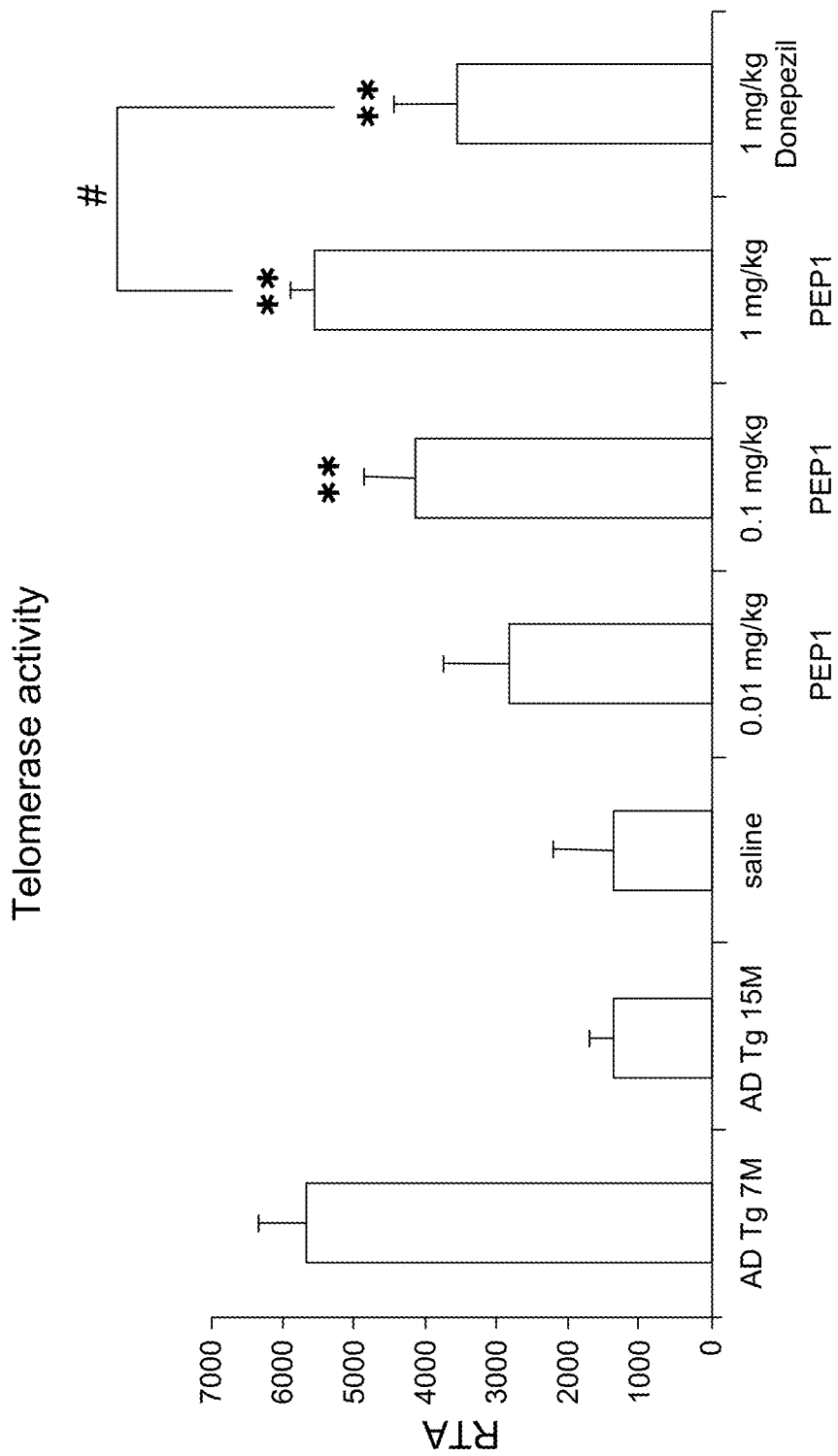
FIG. 1 is a graph showing a result of comparing, when a neurodegenerative disease is induced, increments of telomerase activity by administration of various concentrations (0, 0.01, 0.1 and 1 mg/kg) of a peptide according to the specification in genetically manipulated animal models for experiments of a neurodegenerative disease.

As the present invention may have various modifications and embodiments, the present invention will be described in further detail below. However, the present invention is not limited to specific embodiments, and it should be understood that the present invention includes all modifications, equivalents and alternatives included in the technical idea and scope of the present invention. To explain the present invention, if it is determined that a detailed description of the related art may obscure the gist of the present invention, the detailed description thereof will be omitted.

A telomere, which is a repetitive genetic material located at each terminus of a chromosome, is known to prevent damage in a corresponding chromosome or binding to a different chromosome. The telomere is gradually shortened with cell divisions, becoming very short after a certain number of cell divisions, and the cell eventually stops being divided and dies. On the other hand, the elongation of telomeres is known to extend the life span of a cell. A telomerase-derived peptide PEP1 has been developed as anticancer agents for various types of cancer including pancreatic cancer, and also identified to be involved in anti-inflammation, antioxidation and cell permeability, and major signaling processes in cells, as well as an anticancer effect. In view of the intracellular functions of PEP1, the possibility of using new indications in addition to its use as an existing anticancer agent has been explored.

The inventors had confirmed that a telomerase-derived peptide has activities of increasing telomerase activity and a telomere length, and thus the present invention was completed. More specifically, in one aspect of the present invention, through an Alzheimer animal model experiment, it was confirmed that telomerase activity and a length of telomere-associated DNA were increased by PEP1 in an experiment on cells extracted from Alzheimer animal models with reduced telomerase activity or shortened length.

In one aspect of the present invention, the peptide of SEQ ID NO: 1 (PEP1), the fragment of the peptide of SEQ ID NO: 1 or the peptide having at least 80% sequence homology with the peptide sequence includes a peptide derived from telomerase, and specifically, *Homo sapiens* telomerase.

The peptide disclosed herein may include peptides having at least 80%, 85%, 90, 95%, 96%, 97%, 98% or 99% sequence homology. In addition, the peptide described herein may include a peptide having a difference in 1 or more amino acids, 2 or more amino acids, 3 or more amino acids, 4 or more amino acids, 5 or more amino acids, 6 or more amino acids, or 7 or more amino acids from the peptide of SEQ ID NO: 1 or fragments thereof.

In one aspect of the present invention, an amino acid change is a property of altering physicochemical properties of a peptide. For example, amino acid changes may be performed to improve the thermal stability of a peptide, alter substrate specificity, and change the optimal pH.

The peptide set forth in SEQ ID NO. 1 is shown in the following Table 1. The "name" in Table 1 below is given to distinguish one peptide from another. In one aspect of the present invention, the peptide set forth in SEQ ID NO: 2 denotes the whole peptide of *Homo sapiens* telomerase. In another aspect of the present invention, the peptide of SEQ ID NO: 1, a fragment thereof or a peptide having at least 80% sequence homology with the peptide sequence includes a "synthetic peptide" synthesized from a peptide present at a corresponding location of the peptides included in the telomerase. SEQ. ID. NO: 2 denotes the full-length amino acid sequence of the telomerase.

TABLE 1

| SEQ ID NO: | Name | Location in telomerase | Sequence | Length |
|---|---|---|---|---|
| 1 | pep1 | [611-626] | EARPALLTSRLRFIPK | 16 aa |
| 2 | | [1-1132] | MPRAPRCRAVRSLLRSHYREVLP LATFVRRLGPQGWRLVQRGDPA AFRALVAQCLVCVPWDARPPPA APSFRQVSCLKELVARVLQRLCE RGAKNVLAFGFALLDGARGGPPE AFTTSVRSYLPNTVTDALRGSGA WGLLLRRVGDDVLVHLLARCAL FVLVAPSCAYQVCGPPLYQLGAA TQARPPPHASGPRRRLGCERAWN HSVREAGVPLGLPAPGARRRGGS ASRSLPLPKRPRRGAAPEPERTPV GQGSWARPGRTRGPSDRGFCVV SPARPAEEATSLEGALSGTRHSHP SVGRQHHAGPPSTSRPPRPWDTP CPPVYAETKHFLYSSGDKEQLRP SFLLSSLRPSLTGARRLVETIFLGS RPWMPGTPRRLPRLPQRYWQMR PLFLELLGNHAQCPYGVLLKTHC PLRAAVTPAAGVCAREKPQGSV AAPEEEDTDPRRLVQLLRQHSSP WQVYGFVRACLRRLVPPGLWGS RHNERRFLRNTKKFISLGKHAKL SLQELTWKMSVRDCAWLRRSPG VGCVPAAEHRLREEILAKFLHWL MSVYVVELLRSFFYVTETTFQKN RLFFYRKSVWSKLQSIGIRQHLKR VQLRELSEAEVRQHREARPALLT SRLRFIPKPDGLRPIVNMDYVVG ARTFRREKRAERLTSRVKALFSV LNYERARRPGLLGASVLGLDDIH RAWRTFVLRVRAQDPPPELYFVK VDVTGAYDTIPQDRLTEVIASIIKP QNTYCVRRYAVVQKAAHGHVR KAFKSHVSTLTDLQPYMRQFVA HLQETSPLRDAVVIEQSSSLNEAS SGLFDVFLRFMCHHAVRIRGKSY VQCQGIPQGSILSTLLCSLCYGDM ENKLFAGIRRDGLLLRLVDDFLL VTPHLTHAKTFLRTLVRGVPEYG CVVNLRKTVVNFPVEDEALGGT AFVQMPAHGLFPWCGLLLDTRT LEVQSDYSSYARTSIRASLTFNRG FKAGRNMRRKLFGVLRLKCHSLF LDLQVNSLQTVCTNIYKILLLQA YRFHACVLQLPFHQQVWKNPTFF LRVISDTASLCYSILKAKNAGMSL GAKGAAGPLPSEAVQWLCHQAF LLKLTRHRVTYVPLLGSLRTAQT QLSRKLPGTTLTALEAAANPALP SDFKTILD | 1132 aa |

The composition including the peptide comprising SEQ ID NO: 1 according to an aspect of the present invention is effective in preventing or treating a disease induced by a decrease in telomerase activity or telomere length or a symptom caused by cell loss and senescence. A disease induced by a decrease in telomerase activity or telomere length includes one or more selected from a neurodegenerative disorder, a degenerative disease of the nervous system, a degenerative disease of the skeletal system, a degenerative disease of the muscular system, a viral infectious disease, and a genetic disease causing accelerated cell mortality. A degenerative disease of the nervous system, which benefits from an increase in telomerase activity, may include any one selected from a brain disease, a spinal cord injury, a peripheral nerve injury, a peripheral nerve disease, amyotrophic lateral sclerosis, dementia, Huntington's disease, Parkinson's disease, Alzheimer's disease, spinal cord cerebellar degeneration, and multiple neuropathy, but the present invention is not limited thereto. Further, a disease condition which benefits from an increase in telomerase activity includes a degenerative joint disease, atherosclerosis, thrombosis, stress-induced cell death, such as heart failure or ischemia, age-related macular degeneration, AIDS, impairment of tissue reprogramming occurring with a genetic disease that causes accelerated cell reprogramming and other degenerative conditions.

The composition increasing telomerase activity according to an aspect of the present invention is effective in promoting treatment of a symptom caused by cell loss and senescence, and has a preferable effect in treatment of one or more symptoms selected from tissue loss due to skin wounds, skin wrinkles, anemia, skin psoriasis, skin darkening, and other acute or chronic skin diseases.

In one aspect, the present invention provides a pharmaceutical composition which includes a peptide comprising an amino acid sequence of SEQ ID NO: 1, a peptide having at least 80% sequence homology with the amino acid sequence or a fragment thereof as an active ingredient to increase telomerase activity and extend a telomere.

The composition according to an aspect of the present invention may be applied to all animals including a human, a dog, a chicken, a pig, a cow, a sheep, a guinea pig, and a monkey.

In one aspect, the present invention provides a pharmaceutical composition which includes a peptide comprising an amino acid sequence of SEQ ID NO: 1, a peptide having at least 80% sequence homology with the amino acid sequence or a fragment thereof to prevent and regenerate loss of nerve cells. The pharmaceutical composition of an aspect of the present invention may be administered orally, intrarectally, transdermally, intravenously, intramuscularly, intraperitoneally, intramedullarly, intrathecally or subcutaneously.

Dosage forms for oral administration may include, but are not limited to, tablets, pills, soft or hard capsules, granules, powders, solutions, and emulsions. Dosage forms for parenteral administration may include, but are not limited to, injections, drips, lotions, ointments, gels, creams, suspensions, emulsions, suppositories, patches or sprays.

The pharmaceutical composition according to one aspect of the present invention may comprise, as needed, additives, such as diluents, excipients, lubricants, binders, disintegrating agents, buffers, dispersants, surfactants, coloring agents, flavors or sweetening agents. The pharmaceutical composition according to one aspect of the present invention may be prepared by a conventional method in the art.

An effective ingredient of the pharmaceutical composition according to an exemplary embodiment of the present invention may vary depending on the age, sex, body weight, pathological state and severity of an administration subject, an administration route or determination of a prescriber. Determination of a dosage based on these factors is within the level of one of ordinary skill in the art, and a daily dose of the pharmaceutical composition according to an exemplary embodiment of the present invention may be, for example, 0.01 μg/kg/day to 10 g/kg/day, specifically, 0.1 μg/kg/day to 1 g/kg/day, and more specifically 0.5 μg/kg/day to 100 mg/kg/day, and may be suitably adjusted when there is a difference in effect according to dose. The pharmaceutical composition according to an aspect of the present invention may be administered 1 to 3 times per day, but the present invention is not limited thereto.

The health functional food composition according to an aspect of the present invention may be prepared in any one formulation selected from a powder, a granule, a pill, a tablet, a capsule, a candy, a syrup and a drink, but the present invention is not limited thereto. When the health functional food composition according to an aspect of the present invention is used as a food additive, the health functional food composition may be added as it is or used together with a different food or food ingredient and thus may be suitably used according to a conventional method. Examples of food to which the health functional food composition may be added may include, but not limited to, meat, bread, candies, snacks, noodles, dairy products, vitamin complex, beverages, tea, and drinks, and include all types of health food in the common sense.

The health functional food composition according to an aspect of the present invention may be produced as food, particularly, functional food. The functional food according to an aspect of the present invention includes an ingredient conventionally added in the production of food, for example, a protein, a carbohydrate, a lipid, a nutrient and a seasoning.

The pharmaceutical composition or health functional food composition according to the present invention may contain the peptide of SEQ ID NO: 1 at 0.1% or more, preferably at a maximum of approximately 10%, more preferably at a maximum of approximately 5% and further more preferably at a maximum of 1% (w/v). Selection of the appropriate concentration is dependent on factors such as a preferable dosage, frequency and a method of delivering an active ingredient.

A cosmetic composition according to an aspect of the present invention is not particularly limited in its formulation, and may have a formulation such as a softening toner, an astringent toner, a nourishing toner, an eye cream, a nourishing cream, a massage cream, a cleansing cream, a cleansing foam, cleansing water, a powder, an essence, or a pack.

The cosmetic composition according to an aspect of the present invention may be prepared in various formulations according to a conventional method of preparing a cosmetic composition. For example, the cosmetic composition may be prepared in formulations such as cosmetic and fragrant products containing the peptide, toners, creams, and lotions, and may be used after being diluted with a conventional liquid cleanser, astringent toner or moisturizing lotion. In addition, the cosmetic composition may include a conventional additive such as a stabilizer, a solubilizer, a vitamin, a pigment or a fragrance, which is generally used in the field of a cosmetic composition.

The formulation of the composition according to an aspect of the present invention is not particularly limited, and may be, for example, a tablet, a granule, a powder, a liquid, or a solid preparation. Each formulation may be prepared by mixing suitably selected components conventionally used in the corresponding field as well as an active ingredient according to a formulation or the purpose of its use without difficulty by one of ordinary skill in the art, and these components can have a synergistic effect with the simultaneous application of other components.

The terms used in the specification are intended to be used to describe specific embodiments rather than to limit the present invention. Terms without numbers in front are not intended to limit the quantity but to represent the presence of at least one item cited herein. The terms "comprising", "having", "including", and "containing" should be interpreted openly (i.e. "including but not limited to").

The mention of a numerical range replaces the mention of individual numbers within the range, and unless cited otherwise, each number is applied to the specification as if individually mentioned in the specification. The end values of all of the ranges are included in the range and can be individually combined.

All methods mentioned in the specification may be performed in a suitable order unless noted otherwise or explicitly contradicted within the context. The use of any one embodiment and all embodiments, or exemplary language (e.g., "such as" or "like to"), unless included in the claims, is used to more clearly describe the present invention rather than to limit the scope of the present invention. Any language herein outside of the claims should not be interpreted as essential to the practice of the present invention. Unless defined otherwise, technical and scientific terms used herein each has a meaning ordinarily understood by those of ordinary skill in the art to which the present invention belongs.

The exemplary embodiments of the present invention include the best mode known to the inventors to perform the present invention. Variations in the exemplary embodiments can become clear to those skilled in the art when reading the descriptions above. It is expected that the inventors suitably use such variations, and embody the present invention by different methods described in the specification. Thus, the present invention, as allowed by the patent law, includes equivalents and all modifications of the gist of the present invention mentioned in the accompanying claims. Moreover, all possible variations with any combination of the above-mentioned components are included in the present invention, unless explicitly stated otherwise or contradicted within the context. Although the present invention is described and shown by exemplary embodiments, those skilled in the art will readily understand that there can be various changes in the form and details without departing from the spirit of the invention and range defined by the claims below.

Hereinafter, the configuration and effects of the present invention will be described in further detail with reference to examples and experimental examples. However, the following examples and experimental examples are merely provided to illustrate the present invention to help in understanding of the present invention, and the scope of the present invention is not limited thereto.

Example 1

Synthesis of Peptide

A peptide of SEQ ID NO: 1 (hereinafter, referred to as "PEP 1") was prepared according to a conventionally known method of solid phase peptide synthesis. Specifically, peptides were synthesized by coupling each amino acid to one other from the C-terminus through Fmoc solid phase peptide synthesis (SPPS) using ASP48S (Peptron, Inc., Daejeon, Korea). Peptides in which the first amino acid at the C-terminus is attached to a resin were used as follows:

$NH_2$-Lys(Boc)-2-chloro-Trityl Resin
$NH_2$-Ala-2-chloro-Trityl Resin
$NH_2$-Arg(Pbf)-2-chloro-Trityl Resin In all amino acid ingredients used in the synthesis of the peptides, the N-terminus was protected with Fmoc, and the residues were protected with Trt, Boc, t-butyl ester (t-Bu), and 2,2,4,6,7-pentamethyl dihydro-benzofuran-5-sulfonyl (Pbf) that can be removed in an acid. Examples of the amino acids are as follows.

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-mercaptoacetic acid.

As a coupling reagent, 2-(1H-benzotriazol-1-yl)-1,1,3,3-tetramethyluronium hexafluorophosphate (HBTU)/N-hydroxybenzotriazole (HOBt)/4-methylmorpholine (NMM) was used. Fmoc deprotection was carried out using 20% piperidine in DMF. To isolate the synthesized peptide from the resin and to remove the protecting group of the residue, a cleavage cocktail [trifluoroacetic acid (TFA)/triisopropylsilane (TIS)/ethanedithiol (EDT)/$H_2O$=92.5/2.5/2.5/2.5] was used.

Each peptide was synthesized by a repeated process of reacting each corresponding amino acid using a state in which the starting amino acid was protected by the amino acid protecting group while being bound to a solid phase scaffold, washing the resulting product with a solvent, and performing deprotection. After being detached from the resin, the synthesized peptide was purified by HPLC, synthesis was confirmed by mass spectrometry (MS), and lyophilization was performed.

Purities of all peptides used in the experiment were 95% or higher, as determined using high-performance liquid chromatography.

A specific process of preparing PEP1 was as follows.

1) Coupling

The amino acid (8 equiv.) protected with the $NH_2$-Lys(Boc)-2-chloro-trityl resin was mixed with the coupling reagent HBTU (8 equiv.)/HOBt (8 equiv.)/NMM (16 equiv.) which were dissolved in DMF, reacted at room temperature for 2 hours, and sequentially washed with DMF, MeOH and DMF.

2) Fmoc Deprotection

20% piperidine in DMF was added to the resulting product, a reaction was performed twice for 5 minutes at room temperature, and then washing was sequentially performed with DMF, MeOH, and DMF.

3) The reactions 1) and 2) were repeated to form a peptide backbone $NH_2$-E(OtBu)-A-R(Pbf)-P-A-L-L-T(tBu)-S(tBu)-R(Pbf)L-R(Pbf)-F-I-P-K(Boc)-2-chloro-trityl resin.

4) Cleavage: The peptide was isolated from the resin by adding a cleavage cocktail to the synthesis-completed peptide resin.

5) After cooling diethyl ether was added to the obtained mixture, the peptide obtained by centrifugation was precipitated.

6) After purification through Prep-HPLC, a molecular weight was determined by LC/MS and lyophilized, thereby preparing a powder.

Example 2

Experimental Materials and Method

Example 2-1: Preparation of Experimental Animal

All animal-related procedures were carried out according to the Guideline for Care and Use of Laboratory Animals in Hanyang University. In all experiments, the number and pain of animal subjects were minimized, and all animals were used once.

PEP1 use herein was prepared according to the method described in Example 1, and other reagents and control materials were genuine products purchased from Sigma Aldrich.

To test the PEP1 therapeutic effect on Alzheimer's disease, Alzheimer transgenic mice (3×Tg-AD) were purchased from Jackson Laboratory. Genetic characteristics of the transgenic mice are shown in Table 2.

TABLE 2

| | |
|---|---|
| Strain Name | B6; 129-Psen1tm1Mpm Tg (APPSwe, tauP301L)1Lfa/Mmjax |
| Common Names | 3xTg-AD |
| Disease | Alzheimer Disease; AD |
| Targeted Mutation | amyloid beta precursor protein (APPSwe), microtubule-associated protein tau (tauP30IL) |
| Genotype | Psen1tm1Mpm/Psen1tm1Mpm Tg (APPSwe, tauP301L)1Lfa |
| Phenotype | amyloid beta deposits, neurofibrillary tangles, abnormal behavior (abnormal learning/memory/conditioning, abnormal contextual conditioning behavior) |

After 8-week-old transgenic mice were provided and acclimated, in order to increase the number of the transgenic mice, the mice were divided into males and females in a ratio of 1:2 and bred in each cage for approximately 7 to 8 days, and then separated. Mice that have been confirmed pregnant after approximately 7 to 8 weeks gave birth after one week and went through the nursing period for 3 weeks. Two weeks later, mature mice were able to be obtained. During the acclimation and the entire experiment, the mice were housed at a temperature of 23±2° C. and a relative temperature of 60±10% on a 12-hour light-dark cycle.

To investigate the effect of PEP1 according to concentration after breeding, experimental animals were divided and then administered experimental materials as follows. As a positive control material, donepezil was used, the experimental animals were divided into five groups, and each group included 10 mice. Administered materials and doses per group are as follows.

Group 1: Saline
Group 2: 0.01 mg/kg ofPEP1
Group 3: 0.1 mg/kg of PEP1
Group 4: 1 mg/kg of PEP1
Group 5: 1 mg/kg of donepezil PEP1, saline and donepezil were subcutaneously injected at each concentration three times a week for 2 months from the 12$^{th}$ month, one month later (at the age of 15 months), the mice (10 mice per group) were anesthetized, and reperfusion was carried out through the heart of each mouse using 0.9% saline to remove blood. Afterward, the brain was extracted, and separated into the hippocampus and the whole brain area, thereby obtaining brain tissue, and the tissue was rapidly frozen using liquid nitrogen.

Example 2-2: Telomerase Activity and Method of Measuring Telomere Length

To confirm decreases in telomerase activity and telomere length over time, brain tissues were obtained from Alzheimer-induced animal models at the age of 7 months and 15 months (represented as AD Tg 7M and AD Tg 15M) by the method of Example 2-1 to measure telomerase activity and a telomere length.

Figures 2, 3:
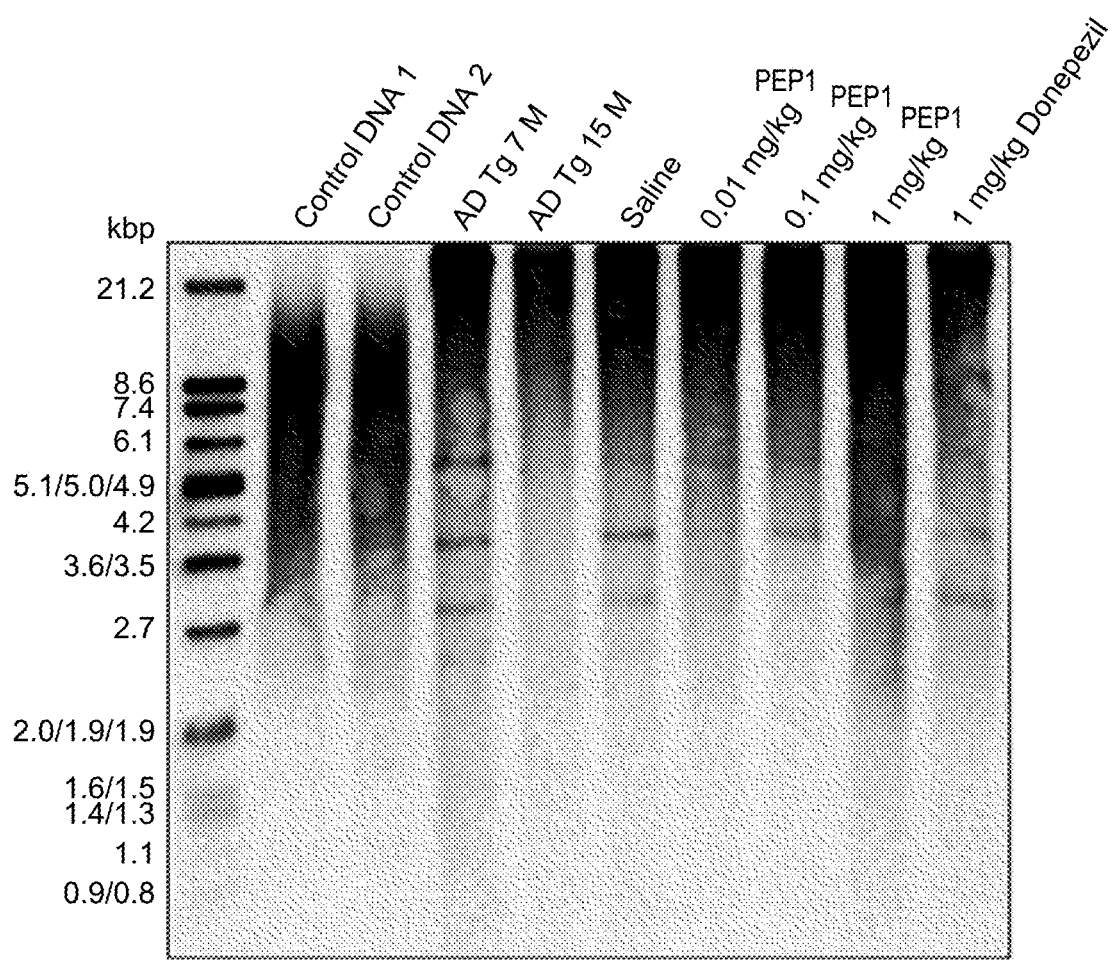
FIG. 2 is a chromosomal electrophoresis image showing, when a neurodegenerative disease is induced, increments of a telomere length by administration of various concentrations (0, 0.01, 0.1 and 1 mg/kg) of a peptide according to the specification in genetically manipulated animal models for experiments of a neurodegenerative disease.
FIG. 3 is a calculation formula for calculating relative telomerase activities (RTAs) measuring telomerase activity.

To investigate PEP1-induced telomerase activity, TeloT-AGGG telomerase PCR ELISAPLUS (Cat #12 013 789 001, Roche Boehringer-Mannheim, IN, USA) was used, the entire brain tissues prepared according to the method of Example 2-1 were pulverized, 200 µl of an ice-cold lysis buffer was added to 2 to 3 g of the tissue, incubated on ice for 30 minutes, and centrifuged at 16,000×g for 20 minutes to isolate 175 µl of a protein. 10 µg of the protein was quantified and mixed with a reaction mixture and an internal standard, followed by PCR (see FIG. 4). Hybridization was carried out, a sample was added to a specially-coated MP module to perform a reaction, and then absorbance was measured at 450 or 690 nm using an ELISA reader. Relative telomerase activities (RTAs) were calculated using a calculation formula (see FIG. 3).

Measurement of a telomere length was performed using a TeloTAGGG telomere length assay (Cat #12 209 136 001, Roche Boehringer-Mannheim, IN, USA), the entire brain tissues were pulverized, and then DNA was extracted using a High Pure PCR Template preparation kit (Cat #11 796 828 001, Roche Boehringer-Mannheim, IN, USA) and mixed with 1 to 2 µg of purified genomic DNA and a Hinfl/Rsa 1 enzyme mixture, and a reaction was performed at 37° C. for 2 hours. After the reaction, the reaction product was mixed with 5 µl of a gel electrophoresis loading buffer 5× and subjected to electrophoresis in a 0.8% agarose gel at a rate of 5 V/cm for 3 hours. When the gel that went through the reaction reacted with an HCL solution for 10 minutes, a bromophenol blue stain turned to yellow. After a sequential reaction of a denaturation solution and a neutralization solution, the resulting products were transferred to a nylon membrane through Southern blotting using 20×SSC for at least 6 to 12 hours. After the Southern transfer, the membrane was baked at 120° C. for 20 minutes to fix DNA to the membrane, thereby hybridizing the membrane washed with the 2×SSC buffer, and image analysis was performed by setting an exposure time to 4 hours using an image analyzer (GE Healthcare, ImageQuant LAS 4000) (see FIG. 5 for analysis formula). Control DNA (represented as control DNA 1 or 2, respectively) for imaging length measurement was random sequence DNA provided in the kit.

Example 2-3: Method for Statistical Verification

For all statistical verification, a SPSS 21 statistics program and the statistics site VassarStats: Website for Statistical Computation (available on the world wide web at: vassarstats.net) were used. Data measured at interval or ratio scales were expressed as mean±S.E.M., for parameter analysis, a one-way or two-way ANOVA test was followed by a Tukey test as a posteriori test, and for non-parametric statistics, a Kruskal-Wallis test and a Mann-Whitney U-test were used. Comparison between groups was performed by a Tukey test. In the case of nominal scales, Chi-square analysis was used to compare groups. When the p-value was less than 0.05, the differences were considered statistically significant.

Example 3

Results of Measuring Telomerase Activity and Telomere Length

Example 3-1: Result of Measuring Telomerase Activity

To determine whether PEP1 increases telomerase activity, telomerase activity was measured through the methods of Examples 2-1 and 2-2. As a result, a PEP-administered (0.1 mg/kg) group (Group 3) showed an increase of 266% compared with a saline-administered group (Group 1), a PEP-administered (mg/kg) group (Group 4) showed an increase of 370% compared with the saline-administered group (Group 1), and showed a statistically significant increase compared with a donepezil-administered (mg/kg) group (Group 5) (see FIG. 1). In addition, it was confirmed that the telomerase activity was decreased in the mice at the age of 15 months (AD Tg 15M), compared with the mice at the age of 7 months (AD Tg 7M).

Example 3-2: Result of Measuring Telomere Length

To confirm whether a PEP1-induced increase in telomerase activity has a direct effect on maintenance of or an increase in telomere length, an experiment for measuring a telomere length was performed through the method of Example 2-2. As a result, like the result of increasing the telomerase activity, the telomere length was increased according to PEP1 administration concentration (see FIG. 2). It can be seen that PEP1 also increases the telomere length, thereby increasing chromosomal stability and a cell protection effect. In addition, it was confirmed that the telomere length was decreased in the mice at the age of 15 months (AD Tg 15M), compared with the mice at the age of 7 months (AD Tg 7M).

Through the above examples, it can be seen that PEP1 has an effect of increasing telomerase activity and a telomere length in experiments using animal models. Therefore, the peptide PEP1 according to an aspect of the present invention may be developed as a material capable of preventing, improving or treating a disease caused by an abnormal decrease in telomerase activity or reduction and loss of a telomere length in cells and a symptom caused by cell senescence, and this material may be used to provide methods of preventing and treating related diseases.

What is claimed is:

1. A method of increasing telomerase activity or extending a telomere length in a patient suffering from a disease caused by a decrease in telomerase activity or telomere length or a symptom caused by cell loss and senescence comprising administering to the patient a composition comprising the isolated peptide of SEQ ID NO: 1 by injection, wherein the disease is one or more selected from a neurodegenerative disorder, a degenerative disease of the nervous system, a degenerative disease of the skeletal system, a degenerative disease of the muscular system, a viral infectious disease, and a genetic disease causing accelerated cell mortality, wherein the degenerative disease of the nervous system is one or more selected from a brain disease, a peripheral nerve injury, a peripheral nerve disease, amyotrophic lateral sclerosis, dementia, Huntington's disease, Parkinson's disease, spinal cord cerebellar degeneration, and multiple neuropathy, wherein the symptom caused by cell loss and senescence include one or more selected from tissue loss caused by skin wounds, skin wrinkles, anemia, and skin darkening.

2. The method according to claim 1, wherein the peptide of SEQ ID NO: 1 is administered at a daily dose of 0.1 μg/kg to 10 g/kg.

3. The method according to claim 1, wherein the peptide of SEQ ID NO: 1 is administered at a daily dose of 0.5 μg/kg to 100 mg/kg.

4. The method according to claim 1, wherein the composition is administered 1 to 3 times per day.

5. The method according to claim 1, wherein the composition is a pharmaceutical composition.

6. The method according to claim 1, wherein the composition is administered through intravenous, intramuscular, or subcutaneous route.

* * * * *